United States Patent
Cronin et al.

(10) Patent No.: US 11,026,613 B2
(45) Date of Patent: Jun. 8, 2021

(54) SYSTEM, DEVICE AND METHOD FOR REMOTELY MONITORING THE WELL-BEING OF A USER WITH A WEARABLE DEVICE

(71) Applicant: KONINKLIJKE PHILIPS N.V., Eindhoven (NL)

(72) Inventors: John E. Cronin, Bonita Springs, FL (US); Steven M. Philbin, Eindhoven (NL); Eric R. Wade, Gainesville, FL (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 121 days.

(21) Appl. No.: 15/555,813

(22) PCT Filed: Mar. 9, 2016

(86) PCT No.: PCT/EP2016/054950
§ 371 (c)(1),
(2) Date: Sep. 5, 2017

(87) PCT Pub. No.: WO2016/142393
PCT Pub. Date: Sep. 15, 2016

(65) Prior Publication Data
US 2018/0042542 A1    Feb. 15, 2018

Related U.S. Application Data

(60) Provisional application No. 62/130,196, filed on Mar. 9, 2015.

(30) Foreign Application Priority Data

Jul. 21, 2015  (EP) .................................. 15177671

(51) Int. Cl.
*A61B 5/00*    (2006.01)
*A61B 5/16*    (2006.01)
(Continued)

(52) U.S. Cl.
CPC ............ *A61B 5/165* (2013.01); *A61B 5/0022* (2013.01); *A61B 5/021* (2013.01); *A61B 5/0205* (2013.01);
(Continued)

(58) Field of Classification Search
CPC ......... A61B 5/16; A61B 5/165; A61B 5/0205; A61B 5/0002; A61B 5/4803;
(Continued)

(56) References Cited

U.S. PATENT DOCUMENTS 4,093,821 A *  6/1978  Williamson ............ G10L 25/90
                                                        600/586
4,543,957 A * 10/1985  Friedman .............. A61B 5/0484
                                                        600/300

(Continued)

FOREIGN PATENT DOCUMENTS

JP    2007296169 A    11/2007
JP    4704952 B2  *   6/2011
(Continued)

OTHER PUBLICATIONS

Cummins et al. "A review of depression of suicide reisk assessment using speech analysis" (Year: 2014).*
(Continued)

*Primary Examiner* — Rex R Holmes
*Assistant Examiner* — Sana Sahand

(57) ABSTRACT

Systems, devices, methods for providing a speech pattern as a metric of well-being system for remotely monitoring the well-being of a patient are disclosed. In one exemplary embodiment, a system can include at least one wearable
(Continued)

device that is configured to collect body sensor data and speech pattern data associated with a patient wearing the device and analyze the data to determine if the patient's emotional well-being is compromised. In some exemplary embodiments, the wearable device can be configured to send an alert to at least one caregiver device that indicates the patient's emotional well-being is compromised. The wearable device can also be configured to send recommendations on courses of action to alleviate the condition.

16 Claims, 18 Drawing Sheets

(51) Int. Cl.
| | | |
|---|---|---|
| *G10L 25/63* | (2013.01) | |
| *A61B 5/021* | (2006.01) | |
| *A61B 5/024* | (2006.01) | |
| *G10L 25/78* | (2013.01) | |
| *A61B 5/0205* | (2006.01) | |
| *G10L 25/84* | (2013.01) | |

(52) U.S. Cl.
CPC ........ *A61B 5/02405* (2013.01); *A61B 5/4803* (2013.01); *A61B 5/4809* (2013.01); *A61B 5/6802* (2013.01); *A61B 5/746* (2013.01); *G10L 25/63* (2013.01); *G10L 25/78* (2013.01); *G10L 25/84* (2013.01); *A61B 5/02438* (2013.01)

(58) Field of Classification Search
CPC ..... A61B 5/0022; A61B 5/4809; A61B 5/746; A61B 5/021; A61B 5/02405; A61B 5/6802; A61B 5/024338; G10L 25/78; G10L 25/84; G10L 25/63
See application file for complete search history.

(56) References Cited

U.S. PATENT DOCUMENTS

| | | | | |
|---|---|---|---|---|
| 6,638,217 | B1 | 10/2003 | Liberman | |
| 6,731,307 | B1* | 5/2004 | Strubbe | G06N 3/004 704/E17.002 |
| 9,058,816 | B2* | 6/2015 | Lech | G10L 17/26 |
| 9,305,140 | B2 | 4/2016 | Federoff | |
| 9,589,107 | B2* | 3/2017 | Bowers | A61B 5/4803 |
| 9,936,914 | B2* | 4/2018 | Quatieri, Jr. | A61B 5/4803 |
| 2004/0210159 | A1* | 10/2004 | Kibar | A61B 5/4803 600/558 |
| 2008/0012701 | A1* | 1/2008 | Kass | A61B 5/0002 340/539.11 |
| 2009/0149778 | A1* | 6/2009 | Naujokat | A61B 5/0002 600/595 |
| 2009/0318773 | A1* | 12/2009 | Jung | G16H 10/20 600/300 |
| 2010/0090834 | A1* | 4/2010 | Buchnick | A61B 5/1117 340/573.1 |
| 2010/0293002 | A1* | 11/2010 | Firminger | G06F 19/3418 705/2 |
| 2012/0116186 | A1* | 5/2012 | Shrivastav | A61B 5/0507 600/301 |
| 2014/0221780 | A1* | 8/2014 | Goldberger | A61B 5/0402 600/301 |
| 2014/0247153 | A1* | 9/2014 | Proud | H04W 4/21 340/870.09 |
| 2014/0377727 | A1* | 12/2014 | Yom-Tov | G06F 16/951 434/236 |
| 2015/0081299 | A1* | 3/2015 | Jasinschi | A61B 5/165 704/246 |
| 2015/0313529 | A1* | 11/2015 | Nevo | A61B 5/165 600/595 |
| 2016/0135737 | A1* | 5/2016 | Bowers | A61B 5/4833 704/270 |
| 2016/0135738 | A1* | 5/2016 | Bowers | A61B 5/4833 600/301 |
| 2016/0317781 | A1* | 11/2016 | Proud | A61M 21/02 |
| 2017/0215782 | A1* | 8/2017 | Ishimaru | A61B 10/00 |

FOREIGN PATENT DOCUMENTS

| | | | |
|---|---|---|---|
| JP | 2012000449 A | * | 1/2012 |
| JP | 2013000408 A | | 1/2013 |
| RU | 53130 U1 | | 5/2006 |
| WO | 2012164534 A1 | | 12/2012 |

OTHER PUBLICATIONS

Faurholt-Jepsen, Maria et al., "Daily electronic self-monitoring of subjective and objective symptoms in bipolar disorder—the MONARCA trial protocol (MONitoring, treAtment and pRediCtion of bipolAr disorder episodes): a randomised controlled single-blind trial", BMJ Open, vol. 3, No. 7, Jul. 2013.

Ozdasm A, Shiavi RG, Wilkes DM, Silverman MK, Silverman SE, "Analysis of vocal tract characteristics for near-term suicidal risk assessment", Methods Inf Med. 2004;43(1):36-8.

\* cited by examiner

| | Sensor readings | | | | | | | |
|---|---|---|---|---|---|---|---|---|
| | Pulse >110 | Pulse <60 | Blood pressure >140mmHg | Blood pressure <90mmHg | Weather sunny | Weather raining | Time of day 12AM-6AM | Time of day 6AM-12AM |
| % Time of speech >30% | Display on user alert GUI "You seem agitated or excited, try to calm down" Send message to caregiver software "User is agitated or excited" | N/A | Display on user alert GUI "Blood pressure high, try taking a break and calm down" Send message to caregiver software "User's blood pressure is high, may need help calming down" | Display on user alert GUI "Blood pressure low, take a break and have something to drink" Send message to caregiver software "User has low blood pressure, needs to rest" | N/A | N/A | Display on user alert GUI "It's late, you should go to bed" | N/A |
| % Time of speech 11-29% | N/A | Send message to caregiver software "User may be lonely" | N/A | N/A | N/A | Send message to caregiver software "User may be depressed" | Send message to caregiver software "User not sleeping through the night" | Send message to caregiver software "User may be lonely" |
| % Time of speech 0-10% | N/A | Send message to caregiver software "User may be lonely" | N/A | Send message to caregiver software "User may be faint" | N/A | Send message to caregiver software "User may be depressed" | N/A | Send message to caregiver software "User has had no interaction" |
| % Interacting with others >40% | Display on user alert GUI "Interaction is agitating or exciting you, try to spend some time alone to calm down" Send message to caregiver software "Possible argument occurring" | N/A | Display on user alert GUI "Interaction is agitating or exciting you, try to spend some time alone to calm down" Send message to caregiver software "Possible argument occurring" | N/A | N/A | N/A | Display on user alert GUI "It's late, you should go to bed" Send message to caregiver software "User staying up late" | N/A |
| % Interacting with others 0-9% | N/A | Send message to caregiver software "User may be lonely" | N/A | Send message to caregiver software "User may be lonely" | N/A | Send message to caregiver software "User may be stuck inside and lonely" | N/A | Send message to caregiver software "User may be lonely" |
| % In front of TV >90% | Display on user alert GUI "TV program is causing your heart to race, try running it off or changing to channel" Send message to caregiver software "User is overly excited from TV, suggest they try something else" | Send message to caregiver software "User may be lonely or bored" | Display on user alert GUI "TV program is causing high blood pressure, try turning it off or changing the channel" | Send message to caregiver software "User may be lonely and bored" | Send message to caregiver software "User may be depressed" | N/A | Display on user alert GUI "It's late, you should go to bed" Send message to doctor "User not sleeping through the night" | N/A |

FIG. 4

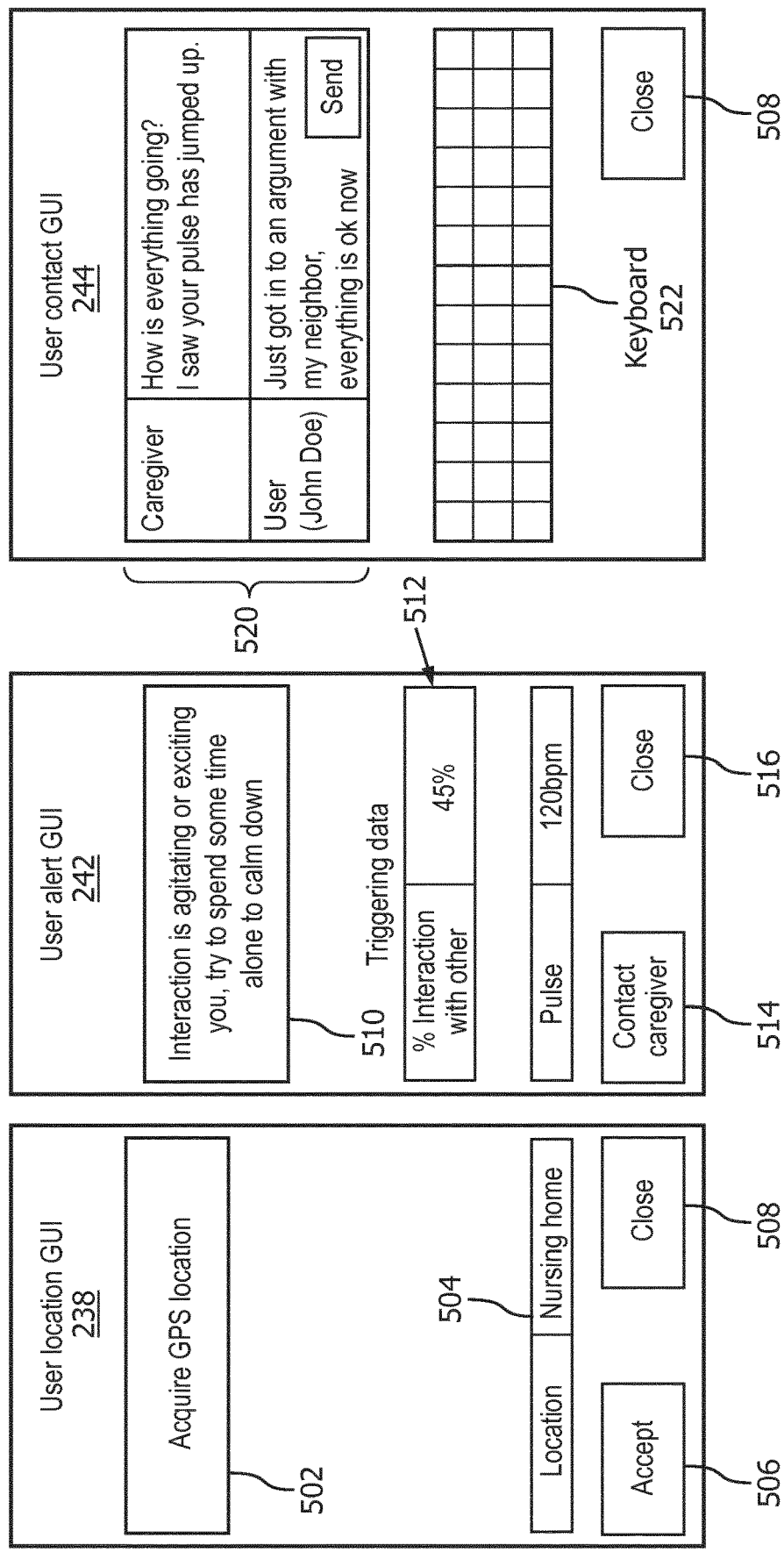

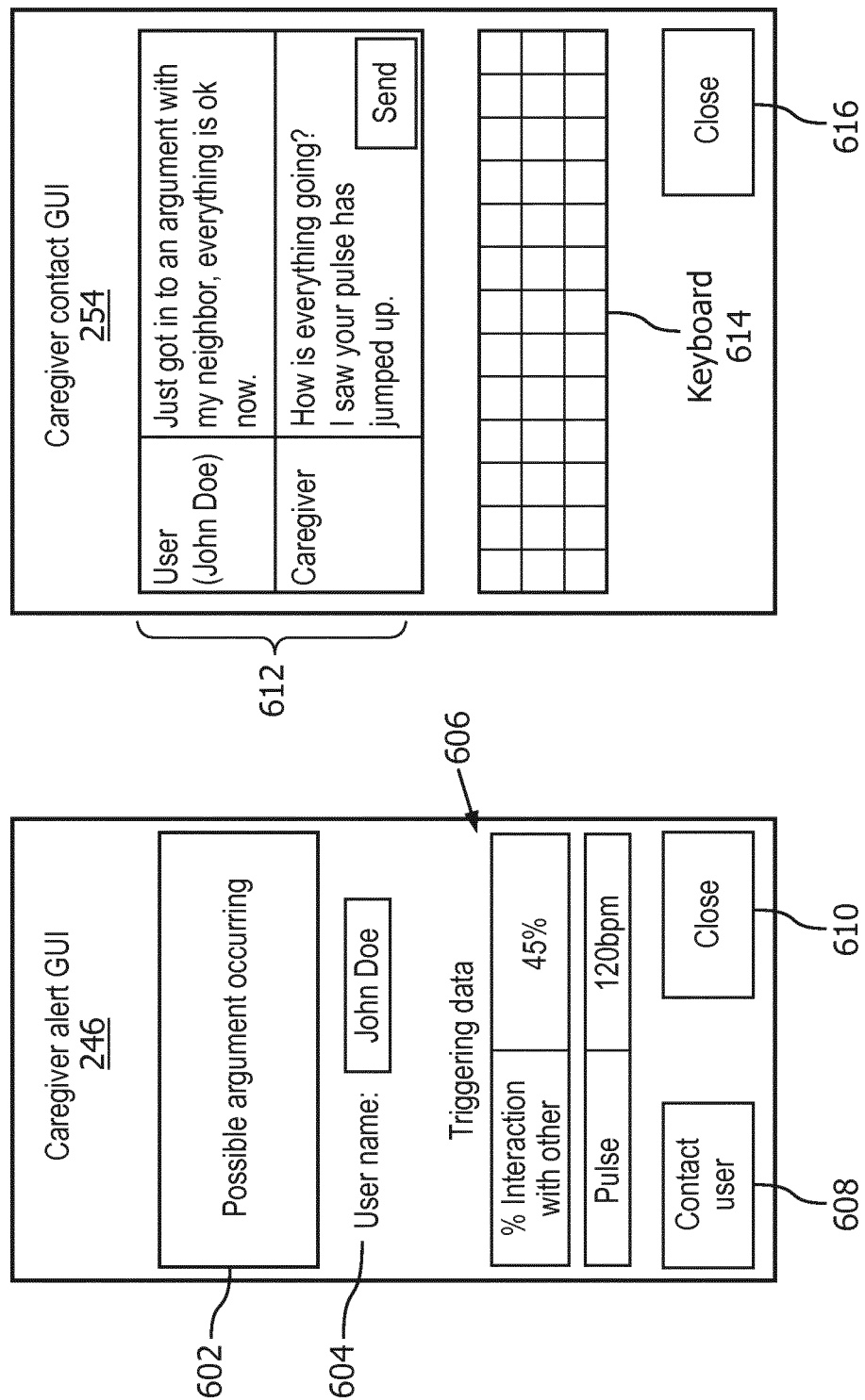

Wearable sensor DB 228

| Date | Time | Pulse | Blood pressure | Weather | Accelerometer | Temperature |
|---|---|---|---|---|---|---|
| 02/02/15 | 08:15:20 | 85bpm | 120/80mmHg | Sunny | 0m/s^2 | 98.6 |
| 02/02/15 | 08:15:40 | 93bpm | 122/80mmHg | Sunny | 0m/s^2 | 98.6 |
| 02/02/15 | 08:16:00 | 102bpm | 123/80mmHg | Sunny | 0m/s^2 | 98.6 |
| 02/02/15 | 08:16:20 | 111bpm | 125/80mmHg | Sunny | 0m/s 2 | 98.6 |
| 02/02/15 | 08:16:40 | 112bpm | 125/80mmHg | Sunny | 0m/s^2 | 98.6 |
| 02/02/15 | 08:17:00 | 112bpm | 125/80mmHg | Sunny | 0m/s^2 | 98.6 |
| 02/02/15 | 08:17:20 | 113bpm | 127/80mmHg | Sunny | 2m/s^2 | 98.6 |
| 02/02/15 | 08:17:40 | 109bpm | 124/80mmHg | Sunny | 4m/s^2 | 98.6 |

FIG. 7A

Wearable speech DB 226

| Date | Time | Type | % Interaction (1 hour) | % Time of speech (1 hour) | % Watching TV (1 hour) |
|---|---|---|---|---|---|
| 02/02/15 | 08:15:20 | Interaction | 23% | 30% | 0% |
| 02/02/15 | 08:15:40 | Interaction | 23% | 30% | 0% |
| 02/02/15 | 08:16:00 | Interaction | 23% | 30% | 0% |
| 02/02/15 | 08:16:20 | Interaction | 23% | 30% | 0% |
| 02/02/15 | 08:16:40 | Interaction | 24% | 31% | 0% |
| 02/02/15 | 08:17:00 | Interaction | 24% | 31% | 0% |
| 02/02/15 | 08:17:20 | Interaction | 24% | 31% | 0% |
| 02/02/15 | 08:17:40 | None | 23% | 30% | 0% |

FIG. 7B

Network location DB 260

| GPS location | Location | GeoFence | Network alert DB |
|---|---|---|---|
| xx101:yy101 | Nursing home | 500 Feet | Nursing home DB |
| xx102:yy102 | Hospital | 10000 Feet | Hospital DB |
| xx103:yy103 | 1 Main street | 100 Feet | 1 Main street DB |
| xx104:yy104 | 2 Main street | 100 Feet | 2 Main street DB |
| xx105:yy105 | 3 Main street | 100 Feet | 3 Main street DB |
| xx106:yy106 | 4 Main street | 150 Feet | 4 Main street DB |
| xx107:yy107 | 5 Main street | 150 Feet | 5 Main street DB |
| ... | ... | ... | ... |

FIG. 8

Network alert DB  258

Nursing home DB  902

| Wearable sensor type | Wearable sensor alert level | Speech type | Speech type level | Action |
|---|---|---|---|---|
| Pulse | >110bpm | Time of speech | >30% for 1 hour | Display on user alert GUI "You seem agitated or excited, try to calm down" Send message to caregiver software "User is agitated or excited" |
| Pulse | >110bpm | Interacting with others | >30% for 1 hour | Display on user alert GUI "Interaction is agitating or exciting you, try to spend some time alone to calm down" Send message to caregiver software "Possible argument occuring" |
| Pulse | >110bpm | In front of TV | >90% for 1 hours | Display on user alert GUI "TV program is causing your heart to race, try turning it off or changing channel" Send message to caregiver software "User is overly excited from TV, suggest they try something else" |

Hospital DB  904

| Wearable sensor type | Wearable sensor alert level | Speech type | Speech type level | Action |
|---|---|---|---|---|
| Pulse | >100bpm | Time of speech | >30% for 1 hour | Display on user alert GUI "You seem agitated or excited, try to calm down" Send message to caregiver software "Patient needs to be calmed down" |
| Pulse | >100bpm | Interacting with others | >30% for 1 hour | Display on user alert GUI "Interaction is agitating or exciting you, try to spend some time alone to calm down" Send message to caregiver software "Possible argument occuring, patient needs to be along" |
| Pulse | >100bpm | In front of TV | >90% for 1 hours | Display on user alert GUI "TV program is causing your heart to race, try turning it off or changing channel" Send message to caregiver software "Make sure patient changes TV channels or turns it off, patient needs to calm down" |

1 Main street

| Wearable sensor type | Wearable sensor alert level | Speech type | Speech type level | Action |
|---|---|---|---|---|
| Pulse | >110bpm | Time of speech | >30% for 1 hour | Display on user alert GUI "You seem agitated or excited, try to calm down" |

FIG. 9

Wearable alert DB  230

Nursing home DB  902

| Wearable sensor type | Wearable sensor alert level | Speech type | Speech type level | Action |
|---|---|---|---|---|
| Pulse | >110bpm | Time of speech | >30% for 1 hour | Display on user alert GUI "You seem agitated or excited, try to calm down" Send message to caregiver software "User is agitated or excited" |
| Pulse | >110bpm | Interacting with others | >30% for 1 hour | Display on user alert GUI "Interaction is agitating or exciting you, try to spend some time alone to calm down" Send message to caregiver software "Possible argument occuring" |
| Pulse | >110bpm | In front of TV | >90% for 1 hours | Display on user alert GUI "TV program is causing your heart to race, try turning it off or changing channel" Send message to caregiver software "User is overly excited from TV, suggest they try something else" |
| Pulse | <60bpm | Time of speech | <10% for 1 hours | Display on user alert GUI "You haven't spoken much lately, want to talk with your caregiver?" Send message to caregiver software "User may be lonely" |
| Pulse | <60bpm | Interaction with others | <10% for 1 hours | Display on user alert GUI "You haven't had much interaction lately, want to talk with your caregiver?" Send message to caregiver software "User may be lonely" |
| Pulse | <60bpm | In front of TV | >90% for 1 hours | Display on user alert GUI "You have been watching a lot of TV, are you bored?" Send message to caregiver software "User may be lonely or bored" |
| Blood pressure | >140mmHG | Time of speech | >30% for 1 hours | Display on user alert GUI "Blood pressure high, try taking a break and calming down" Send message to caregiver software "User's blood pressure is high, may need help calming down" |
| Blood pressure | >140mmHG | Interaction with others | >30% for 1 hours | Display on user alert GUI "Interaction is agitating or exciting you, try to spend some time alone to calm down" Send message to caregiver software "Possible argument occurring" |
| ooo | ooo | ooo | ooo | ooo |

FIG. 10

SYSTEM, DEVICE AND METHOD FOR REMOTELY MONITORING THE WELL-BEING OF A USER WITH A WEARABLE DEVICE

This application is the U.S. National Phase application under 35 U.S.C. § 371 of International Application No. PCT/EP2016/054950, filed on Mar. 9, 2016, which claims the benefit of European Application No. 15177671.3, filed Jul. 21, 2015, and Provisional Application Ser. No. 62/130,196, filed Mar. 9, 2015. These applications are hereby incorporated by reference herein.

TECHNICAL FIELD

The present invention generally relates to the field of wearable devices. In particular, the present invention is directed to wearable devices having speech pattern as a metric of well-being functionality, as well as related systems and methods.

BACKGROUND

Wearable electronic devices, or as used herein, wearable technology is a new class of electronic systems that can provide data acquisition through a variety of unobtrusive sensors that can be worn by a user. The sensors gather information, for example, about the environment, the user's activity, or the user's health status. However, there are significant challenges related to the coordination, computation, communication, privacy, security, and presentation of the collected data. Additionally, there are challenges related to power management given the current state of battery technology. Furthermore, analysis of the data is needed to make the data gathered by the sensors useful and relevant to end-users. In some cases, additional sources of information can be used to supplement the data gathered by the sensors. The many challenges that wearable technology presents require new designs in hardware and software.

Caregivers are often unable to develop an accurate assessment of their patients' emotional well-being. For example, because caregivers can only visit with each patient for a limited period of time, caregivers have a limited amount of information for assessing wellbeing. Also, patients can consciously or inadvertently withhold information from their caregivers for a variety of reasons, including the social stigma associated with emotional well-being illnesses such as depression and anxiety, or from the patient not fully recognizing the illness they are suffering from. In addition, the effectiveness of the care that caregivers provide is lessened when it is administered long after an event that caused a decrease in emotional well-being has occurred.

SUMMARY OF THE DISCLOSURE

Aspects of the present disclosure include systems, devices, and methods for remotely monitoring the emotional well-being of a patient with a wearable device. In some embodiments, the wearable device can have a speech sensor and body sensors and the method can include correlating speech patterns and other audio data with one or more additional sensor readings from the body sensors to detect poor emotional well-being. By correlating user speech data with other body sensor readings, a wearable device can accurately and quickly detect a variety of different emotional illnesses, such as depression, anxiety, and stress, thereby providing a caregiver with a more accurate assessment of patient emotional well-being and enabling prompt treatment of the emotional illness. Such devices and methods can also assist in identifying external stimuli that can be contributing to a patient's poor emotional health so that a caregiver can remove the negative external stimuli from the patient's surroundings.

A first aspect of the current invention is directed to a method of remotely monitoring emotional well-being of a user with a wearable device having a speech sensor and body sensors. The method includes monitoring speech pattern data from the speech sensor; monitoring body sensor data from the body sensors; comparing the speech pattern data and the body sensor data to an alert database having a plurality of emotional well-being alerts; and sending an alert message to a caregiver when the speech pattern data and the body sensor data trigger at least one of the emotional well-being alerts.

Another aspect of the current invention is directed to a system a system for remotely monitoring the emotional well-being of a user, including at least one wearable device having a speech sensor for sensing speech pattern data and one or more body sensors for sensing body sensor data, one or more computing devices having data processor(s) for collecting and monitoring data. The wearable device(s) is configured to collect and monitor speech pattern data from the speech sensor and/or collect and monitor body sensor data from the body sensor (s). One or more computing devices are configured to compare the speech pattern data and/or the body sensor data to data from one or more databases having a plurality of emotional well-being alerts, and determine whether to trigger one or more emotional well-being alerts based on the comparison. The wearable device is also structured and configured store, display, indicate and/or send an alert message when one or more of the emotional well-being alerts are triggered.

Yet another aspect of the current invention is directed to a system a wearable device for remotely monitoring the emotional well-being of a user, including a speech sensor for sensing speech pattern data, one or more body sensors for sensing body sensor data, one or more computing devices having data processor(s) for collecting and monitoring data, and a communication module for sending and/or receiving data. The computing device(s) are configured to collect and monitor speech pattern data from the speech sensor and/or collect and monitor body sensor data from the body sensor(s). The computing device(s) are further configured to compare the speech pattern data and/or the body sensor data to data from one or more databases having a plurality of emotional well-being alerts, and determine whether to trigger at least one of the emotional well-being alerts based on the comparison. The communication module is configured to transmit an alert message when at least one of the emotional well-being alerts are triggered.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 4 shows an exemplary alert matrix that shows example alerts that can be generated by the wearable monitoring software, according to an embodiment of the present invention;

FIG. 5A shows an exemplary user location graphical user interface (GUI), according to an embodiment of the present invention;

FIG. 5B shows an exemplary user alert GUI, according to an embodiment of the present invention;

FIG. 5C shows an exemplary user contact GUI, according to an embodiment of the present invention;

FIG. 6A shows an exemplary caregiver alert GUI, according to an embodiment of the present invention;

FIG. 6B shows an exemplary caregiver contact GUI, according to an embodiment of the present invention;

FIG. 7A shows an exemplary wearable sensor database, according to an embodiment of the present invention;

FIG. 7B shows an exemplary wearable speech database, according to an embodiment of the present invention;

FIG. 8 shows an exemplary network location database, according to an embodiment of the present invention;

FIG. 9 shows an exemplary network alert database including Nursing Home, Hospital, and 1 Main Street alert databases, according to an embodiment of the present invention;

FIG. 10 shows an exemplary wearable alert database, according to an embodiment of the present invention;

DETAILED DESCRIPTION OF EXEMPLARY EMBODIMENTS

The present disclosure includes systems, devices and methods for providing a speech pattern as a metric of a well-being system for remotely monitoring the well-being of a patient. In one exemplary embodiment, the system can include at least one wearable device that is configured to collect body sensor data and speech pattern data associated with a patient and analyze the data to determine if the patient's well-being is compromised and that an alert should be issued. In some exemplary embodiments, the wearable device can be configured to send an alert to at least one caregiver device that indicates the patient's well-being is compromised. The device can also be configured to send recommendations on courses of action to alleviate the condition. In some embodiments, the alert can also include specific information relating to the alert, including the specific manner in which the patient's well-being is compromised and the sensor data that gave rise to the alert. Such systems and devices can be used in a variety of caregiving settings, such as settings where it is difficult for a caregiver to obtain accurate information on the well-being of a patient, such as a patient that is remote from a caregiver or a patient that is reluctant to tell the caregiver how they are really feeling. For example, caregivers of senior citizens, including the children of senior citizens and nursing home officials can utilize embodiments of the present disclosure to gain accurate and real-time information on the well-being of their parents or guests, respectively.

Figure 1:
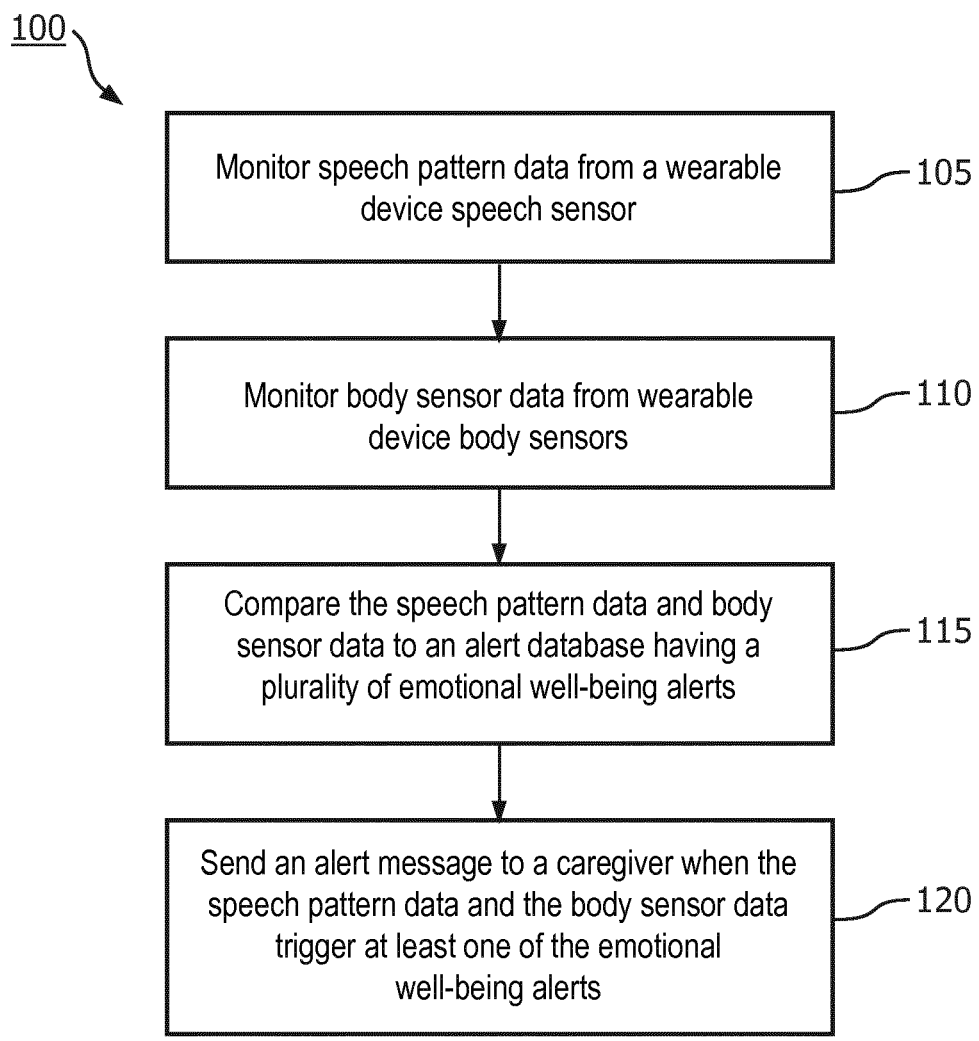
FIG. 1 shows an example method for sending an alert to a caregiver device with a wearable device, according to an embodiment of the present invention.

FIG. 1 illustrates exemplary method 100 of remotely monitoring the emotional well-being of a patient with a wearable device having a speech sensor and body sensors. In one embodiment, the method can include, at step 105, monitoring speech pattern data from the speech sensor, and at step 110, monitoring body sensor data from the body sensors. As discussed below, an exemplary wearable device can include a variety of body sensors, one or more microphones, and software with instructions for receiving data from the sensors and processing the data to obtain various metrics that can be used to monitor a user's emotional well-being. As shown, the method can also include, at step 115, comparing the speech pattern data and the body sensor data to an alert database having a plurality of emotional well-being alerts. And at step 120, the method can include sending an alert message to a caregiver when the speech pattern data and the body sensor data trigger at least one of the emotional well-being alerts, indicating the user's emotional well-being is compromised.

Figure 2:
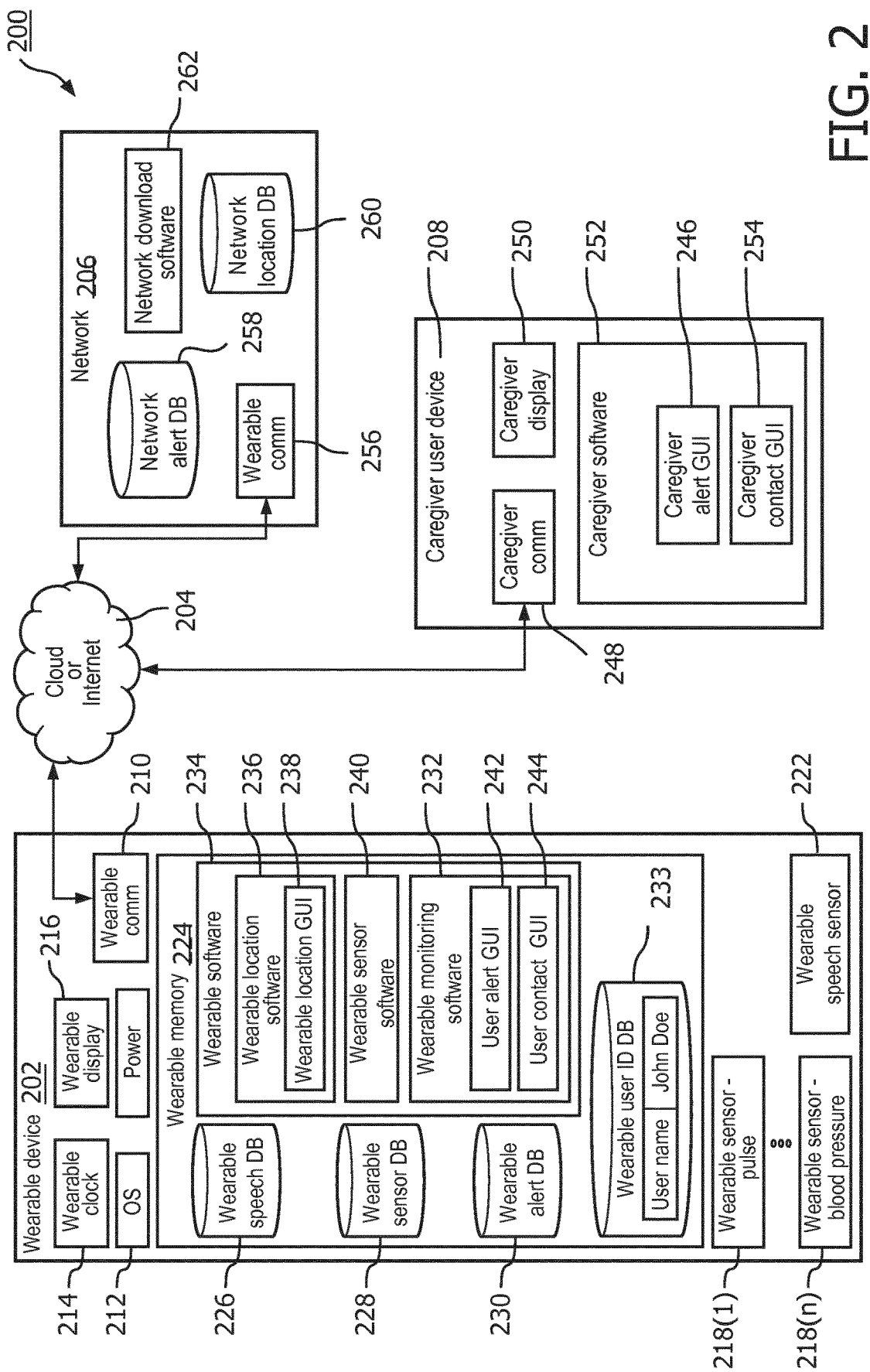
FIG. 2 shows an exemplary speech pattern as a metric of well-being system, according to an embodiment of the present invention.

FIG. 2 illustrates an exemplary speech pattern as a metric of a well-being system 200 for implementing aspects of the present disclosure. As shown, exemplary system 200 can include one or more wearable devices 202 connected, e.g., via the "cloud" or Internet 204, to a network 206 and one or more caregiver user devices 208. As shown, wearable device 202 can include a communications module 210 for communicating with the network and caregivers via, for example, the cloud or Internet 204 by any communications means, including Wi-Fi™, Bluetooth™, 4G LTE, cellular data etc. Wearable device 202 can have an operating system 212 ("OS"), a clock 214 and display 216, e.g., touch display, and can also have a plurality of sensors, such as pulse sensors 218, blood pressure sensors 220, speech sensors 222 such as microphones for speech sensing, and sensors for determining weather conditions, and/or functionality for obtaining weather information from an external source. Wearable device 202 can also include a memory 224 that, as illustrated, can store a variety of software programs and databases. The exemplary wearable device memory databases can include a speech database 226 for storing recorded speech data, a sensor database 228 for storing data from sensors other than speech sensors, and an alert database 230 which can include various predetermined combinations of sensor data and speech pattern data that suggest a patient's wellbeing is compromised and an alert is required. The alert database 230 information can be compared to sensor data by, for example, the monitoring software 232, for determining if an alert condition has occurred. Wearable device 202 can also include a user ID database 233 for storing user ID information.

Wearable device 202 can also include a variety of software programs 234, including location software 236 for providing current location information to a user and that can also transmit user location data to network 206 for obtaining location-specific alert data. Location software 236 can also include software for an associated wearable location graphical user interface 238 (GUI). Device software 234 can also include sensor software 240 for operating the various wearable device sensors 218(1)-218(n) and speech sensor(s) 222 and storing sensor data and speech pattern data in the sensor and speech databases, and monitoring software 232 for monitoring sensor data and speech pattern and other audio data, and comparing the data to other information, such as the information in wearable alert database 230, for determining if an alert is needed. In some examples, wearable sensor software 240 can include instructions for processing and analyzing audio from wearable speech sensor(s) 222, e.g., one or more microphones located on or otherwise operably connected to wearable device 202, for determining user speech patterns. In one example, software 240 can include algorithms known in the art for isolating a user's speech from ambient sounds. In one example, wearable software 240 can also be configured to analyze various aspects of the user speech substantially in real-time to determine if the user is involved in a normal conversation, or if the user speech indicates the user is yelling or otherwise in an argument. In some examples, software 240 can also have instructions for analyzing ambient audio isolated from user speech, if any, and further process the ambient audio to identify the speech of others, including people in the vicinity of the user, as well as speech and other sounds from radios, computers, and televisions. In one example, software 240 can be configured to analyze frequencies and other characteristics of the user speech and the speech of others to determine if the relative frequency indicates the user is involved in a conversation with another person.

In some examples, wearable sensor software 240 can also include software for processing data from the wearable body sensors 218(1)-218(n), e.g., pulse and blood pressure sensors, to determine a rate of change in the sensor reading, to correlate various sensor readings to cross reference and analyze sensor data, and to calculate various metrics, such as heart rate variability (HRV). As described below, the body sensors 218(1)-218(n) can also include one or more movement sensors, such as accelerometers, which can be used to record user movement for a variety of reasons, including determining when the user is awake and for monitoring a user's physical activity levels. Monitoring software 232 can contain instructions for a user alert GUI 242 for displaying one or more user alerts on wearable device display 216 and for optionally displaying the triggering data that gave rise to an alert. Monitoring software 232 can also provide a user contact GUI 244 for allowing a user to contact a caregiver. Monitoring software 232 can also be configured to cause wearable device 202 to transmit information, including warnings, to one or more caregiver user devices 208 for display in the caregiver alert GUI 246.

The example caregiver user device(s) 208 can similarly include a communications module 248 and display 250 and can also include software 252 including instructions for a caregiver alert GUI 246 which can display alerts received from wearable device 202 and can optionally also display the triggering data that gave rise to the alert. Caregiver user device 208 can also include a caregiver contact GUI 254 for allowing a caregiver to contact a user. Exemplary system 200 can also include network 206 for providing location-specific alert settings to wearable device 202. Exemplary network 206 can include a communications module 256 for communicating with wearable devices 202, a network alert database 258 that, as described more below, can include a plurality of alert databases for specific geographic locations and for specific users, a network location database 260 that includes geolocation information for the plurality of locations in network alert database 258, and network location software 262 for operating the network alert and location databases and for causing communication module 256 to send and receive information from wearable devices 202. In alternative embodiments, speech pattern as a metric of well-being systems made in accordance with the present disclosure cannot include the illustrated network, and wearable devices can contain all alert database information, including location specific information, locally on the device.

Figure 3:
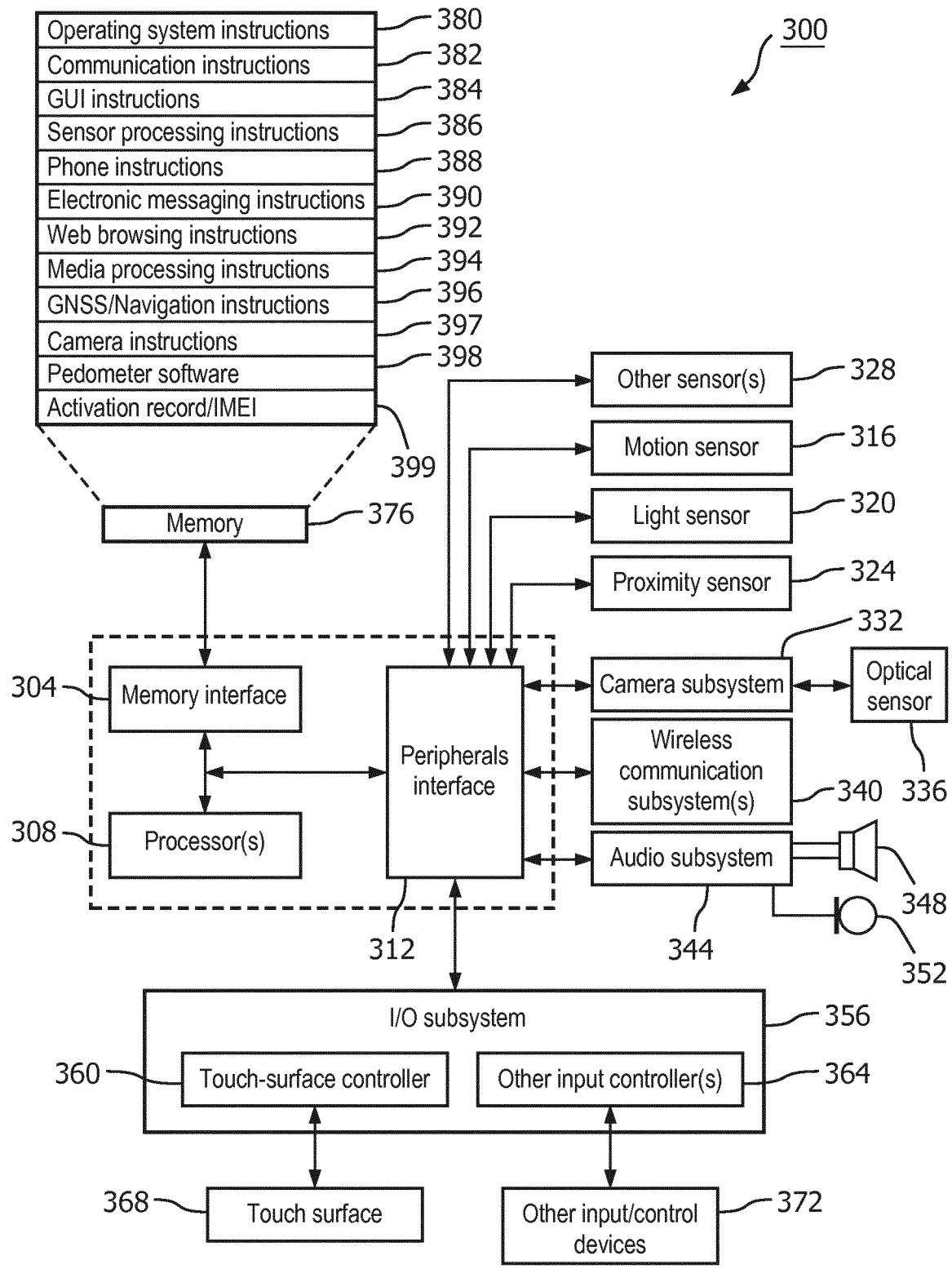
FIG. 3 is a block diagram of an exemplary architecture and functionality of a computing device that can be incorporated in a wearable device, according to an embodiment of the present invention.

FIG. 3 is a block diagram of an exemplary wearable computing device 300 that can be configured to implement any one or more of various features and/or processes of the present disclosure, such as the features and processes illustrated in other figures of this disclosure, as well as features and processes that would be apparent to those of ordinary skill in the art after reading this entire disclosure. As shown, computing device 300 can include a memory interface 304, one or more data processors, image processors and/or central processing units 308, and a peripherals interface 312. Memory interface 304, one or more processors 308, and/or peripherals interface 312 can be separate components or can be integrated in one or more integrated circuits. The various components in computing device 300 can be coupled by one or more communication buses or signal lines.

Sensors, devices, and subsystems can be coupled to peripherals interface 312 to facilitate one or more functionalities. For example, a motion sensor 316, a light sensor 320, and a proximity sensor 324 can be coupled to peripherals interface 312 to facilitate orientation, lighting, and/or proximity functions. Other sensors 328 can also be connected to peripherals interface 312, such as a global navigation satellite system (GNSS) (e.g., GPS receiver), a temperature sensor, a biometric sensor, and/or one or more other sensing devices, to facilitate related functionalities.

A camera subsystem 332 and an optical sensor 336, e.g., a charged coupled device (CCD) or a complementary metal-oxide semiconductor (CMOS) optical sensor, can be utilized to facilitate camera functions, such as recording images and/or video. Camera subsystem 332 and optical sensor 336 can be used to collect images of a user to be used during authentication of a user, e.g., by performing facial recognition analysis.

Communication functions can be facilitated through one or more wireless communication subsystems 340, which can include radio frequency receivers and transmitters and/or optical (e.g., infrared) receivers and transmitters. The specific design and implementation of communication subsystem 340 can depend on the communication network(s) over which computing device 300 is intended to operate. For example, computing device 300 can include communication subsystems 340 designed to operate over a GSM network, a GPRS network, an EDGE network, a Wi-Fi™ or WiMax™ network, and/or a Bluetooth™ network. In particular, wireless communication subsystems 340 can include hosting protocols such that one or more devices 300 can be configured as a base station for other wireless devices.

An audio subsystem 344 can be coupled to a speaker 348 and a microphone 352 to facilitate voice-enabled functions, such as speaker recognition, voice replication, digital recording, and/or telephony functions. Audio subsystem 344 can be configured to facilitate processing voice commands, voice-printing, and voice authentication.

I/O subsystem 356 can include a touch-surface controller 360 and/or other input controller(s) 364. Touch-surface controller 360 can be coupled to a touch surface 368. Touch surface 368 and touch-surface controller 360 can, for example, detect contact and movement or a lack thereof using one or more of any of a plurality of touch sensitivity technologies, including but not limited to capacitive, resistive, infrared, and/or surface acoustic wave technologies, optionally as well as other proximity sensor arrays and/or other elements for determining one or more points of contact with touch surface 368.

Other input controller(s) 364 can be coupled to other input/control devices 372, such as one or more buttons, rocker switches, thumb-wheel, infrared port, USB port, and/or a pointer device such as a stylus. One or more related buttons or other controls (not shown) can include one or more sets of up/down buttons for volume and/or amplitude control of speaker 348 and/or microphone 352. Using the same or similar buttons or other controls, a user can activate a voice control, or voice command, module that enables the user to speak commands into microphone to cause device 300 to execute the spoken command. The user can customize functionality of one or more buttons or other controls. Touch surface 368 can, for example, also be used to implement virtual or soft buttons and/or a keyboard.

In some implementations, computing device 300 can present recorded audio and/or video files, such as MP3, AAC, and/or MPEG files. In some implementations, computing device 300 can include the functionality of an MP3 player, such as an iPod™. Computing device 300 can, therefore, include a 36-pin connector that is compatible with related iPod™ hardware. Other input/output and control devices can also be used.

As shown, memory interface 304 can be coupled to one or more types of memory 376. Memory 376 can include high-speed random access memory and/or non-volatile memory, such as one or more magnetic disk storage devices, one or more optical storage devices, and/or flash memory (e.g., NAND, NOR). Memory 376 can store an operating system 380, such as Darwin™, RTXC, LINUX, UNIX, OS X™, WINDOWS™, and/or an embedded operating system such as VxWorks. Operating system 380 can include instructions for handling basic system services and/or for performing hardware dependent tasks. In some implementations, operating system 380 can comprise a kernel (e.g., UNIX kernel). Further, in some implementations, operating system 380 can include instructions for performing voice authentication.

Memory 376 can also store communication instructions 382 to facilitate communicating with one or more additional devices, one or more computers, and/or one or more servers. Additionally or alternatively, memory 376 can include: graphical user interface instructions 384 to facilitate graphic user interface processing; sensor processing instructions 386 to facilitate sensor-related processing and functions; phone instructions 388 to facilitate phone-related processes and functions; electronic messaging instructions 390 to facilitate electronic-messaging related processes and functions; web browsing instructions 392 to facilitate web browsing-related processes and functions; media processing instructions 394 to facilitate media processing-related processes and functions; GNSS/Navigation instructions 396 to facilitate GNSS and navigation-related processes and instructions; and/or camera instructions 397 to facilitate camera-related processes and functions. Memory 376 can store other software instructions 398 to facilitate other processes and functions. For example, other software instructions 398 can include instructions for counting steps the user takes when device 300 is worn.

Memory 376 can also store other software instructions (not shown), such as web video instructions to facilitate web video-related processes and functions and/or web shopping instructions to facilitate web shopping-related processes and functions. In some implementations, media processing instructions 394 can be divided into audio processing instructions and video processing instructions to facilitate audio processing-related processes and functions and video processing-related processes and functions, respectively. An activation record and International Mobile Equipment Identity (IMEI) 399 or similar hardware identifier can also be stored in memory 376.

Each of the above identified instructions and applications can correspond to a set of instructions for performing one or more functions described herein. These instructions need not necessarily be implemented as separate software programs, procedures, or modules. Memory 376 can include additional instructions or fewer instructions. Further, various functions of computing device 300 can be implemented in hardware and/or in software, including in one or more signal processing and/or application specific integrated circuits.

FIG. 4 shows an exemplary alert matrix 400 that shows example alerts that can be generated by wearable monitoring software 232 for display on at least one of the user alert GUI 242 and caregiver alert GUI 246 s when a combination of sensor data received by the monitoring software matches one or more of the combinations shown in FIG. 4. Thus, an alert matrix 400, such as the alert matrix shown in FIG. 4, can be used to identify a combination of two indications that, when they are occurring at the same time, suggest an undesirable condition, where intervention by one or more of the wearable devices 202, via user alert GUI 242, and one or more caregivers, is desired. As shown, the illustrated example alert matrix 400 includes various speech sensor data categories along the left-hand-column and other non-speech data types along the top-most row and each alert is based on a specific combination of a speech sensor reading with another sensor reading, such as heart rate, blood pressure, weather, and time of day. As will be appreciated, in other embodiments, alerts can be based on the combination of data from more than two sensor types, such as, for example, a three-dimensional, or higher-dimension matrix, where an alert is based on the combination of three or more data types and/or values. Also, some alerts can be based on a combination of sensor data that does not include speech sensor data.

In one example, an alert database can include one or more depression alerts that, when triggered, indicate the user can be suffering from depression. In one example, the depression alerts can broadly include a variety of different alerts that include an indication of mild loneliness through severe depression. FIG. 4 illustrates examples of depression alerts, including combinations of lower levels of speaking time, time spent interacting with others, or higher levels of time in front of a TV, combined with a reading from a body sensor that is below a predetermined value, including a pulse rate below a minimum pulse value, e.g., 60 bpm, and user blood pressure below a minimum blood pressure value, e.g., 90 mmHG. As will be appreciated, these minimum values are provided merely by way of example and can be varied, for example, to tailor the alert to the user's specific baseline vitals, or, as described more below, to tailor the alerts to specific geographic locations so the sensitivity of wearable device 202 can be tuned based on user location. Other examples of depression alerts include minimal speaking combined with a weather value received by or sensed by the wearable device indicating poor weather, such as cloudy or raining, or combined with time of day. Further, other depression alerts can include combining an indication of low levels of speaking with a low HRV which can be calculated from the pulse rate by wearable software 334. In one example, wearable software 234 can include instructions for calculating a non-interaction value based on the percent of time the user has not spoken and the depression alerts can be triggered by specific combinations of non-interaction values and other data. In one example, the non-interaction values can include factors in addition to the raw non-interaction time detected by the speech sensor, including factors for normalizing the percent of speaking or interaction to a normal baseline value associated with the user. In another example, different factors can be applied depending on the type of non-interaction, e.g., time not speaking with others but spent walking or exercising versus time spent not speaking to others and watching TV. In yet another example, wearable device 202 can be configured to determine if the user is awake and not include speech pattern data during periods the user is asleep in the calculation of the non-interaction value. In one example, wearable software 234 can include instructions that assume the user is asleep during a nighttime period unless device 202 receives a signal indicating the user is awake, such as user movement from a wearable movement sensor, or audio from the wearable speech sensor indicating the user is awake, such as user speech, or ambient sounds such as television, radio, or computer sounds. In one example, wearable device 202 can also prompt the user asking the user if he or she is awake if it is nighttime and the device detects ambient sounds.

Exemplary well-being alerts can also include one or more stress alerts that, when triggered, indicate the user is under stress or is otherwise overly-excited. FIG. 4 illustrates example stress alerts that can include a percent of time speaking or interacting with others combined with a reading from at least one body sensor that is greater than a maximum value. Exemplary body sensor readings can include a pulse rate above a maximum pulse value, e.g., 100 bpm, and blood pressure above a maximum blood pressure value, e.g., 140 mmHG. As will be appreciated, these maximum values are provided merely by way of example and can be varied, for example, to tailor the alert to the user's specific baseline vitals, or, as described more below, to tailor the alerts to specific geographic locations so the sensitivity of the wearable device can be tuned based on user location. In other examples, stress alerts can include alerts that are triggered when the wearable speech sensors 222 detect any of the speech types discussed herein at the same time that a rate of change in one or more body sensor readings is greater than a maximum rate of change. In yet another example, stress alerts can be triggered by contemporaneous or recent onset of a detected sound with a rate of change in a body sensor reading above a maximum rate of change.

As the term is used herein, stress and depression alerts can also include sleep disorder alerts since sleep disorders can often be caused by varying degrees of stress or loneliness or depression. In the example shown, sleep related alerts can include a detection of a specific sound or speech pattern, e.g., a percent of time speaking, or interacting with others, or watching TV, during a nighttime period. As discussed above in connection with the depression alerts, wearable device 202 can be configured to verify the user is awake prior to generating sleep-disorder related depression or stress alerts.

FIGS. 5A-5C show three exemplary GUIs that can be included in wearable device 202 made in accordance with the present disclosure. As shown in FIG. 5A, wearable device 202 can include a user location GUI for confirming a user's current location. As shown, the location GUI can include an "Acquire GPS Location" button 502 for receiving a request from a user to determine a current location, and a location field 504, which can display what the wearable device has determined to be a current location. As described more below, in some embodiments, the current location information can be received from network location database 260 in response to wearable device 202 sending current geolocation information to network 206. In some embodiments, location GUI 238 can also include an accept button 506 for allowing a user to send confirmation to the network 206 that the displayed current location is accurate, and in response, the network 206 can send the appropriate alert database 230 to wearable device 202. GUI 238 can also include close button 508 for closing the user location GUI. As shown in FIG. 5B, the device can also include a user alert GUI for displaying an alert to a user of wearable device 202. The example GUI can include a text box 510 for displaying the alert text that notifies the user that his or her emotional well-being can be compromised and can also display a recommendation for improving the user's emotional well-being. In the illustrated example, the alert is an example of a stress alert based on a determination of a stressed or agitated state based on the combination of a percent of time the user has been interacting with someone and a pulse reading that is greater than a maximum pulse value associated with the stress alert. User alert GUI 242 can also display 512 a message that identifies the conversation as the potential source of the user's stress and a recommendation to alleviate the stress, here, to spend some time alone to calm down. User alert GUI 242 can also include a triggering data display 512, which can show the sensor data that gave rise to the alert. In the example, the triggering data includes a percent interaction with another person and a heart rate or pulse. User alert GUI 242 can also include a contact caregiver button 514 that, if selected, can execute the user contact GUI 244 for contacting the caregiver, and a close button 516 for closing the alert GUI. FIG. 5C shows an exemplary user contact GUI 244 that, in the illustrated example, is a texting program for communicating with a caregiver, including windows 520 for displaying text messages and a virtual keyboard 522. In other examples, user contact GUI 244 can also include phone (including cellular, Internet based, etc.), video, and email capability for providing additional communication options. GUI 244 can also include close button 524 for closing the user contact GUI.

FIGS. 6A and 6B show exemplary caregiver device GUIs, including an alert GUI 246 and a contact GUI 254. The exemplary alert GUI 246 can include features that are similar to wearable device user alert GUI 242, including a text box 602 for displaying an alert message. In the illustrated example, rather than display the same message displayed on user device, the alert message on the caregiver device 208 can instead be tailored for a caregiver. The illustrated example is a short message indicating a possible argument is occurring. In alternative examples, additional information can be provided, such as associated medical information and/or patient-specific alert history. As shown, the caregiver alert GUI 246 can also include a user name 604 identifying the user or patient the alert is associated with, as well as triggering data 606 showing the sensor data that gave rise to the alert, and a contact user button 608 for executing the caregiver contact GUI 254, as well as a close button 610 for closing the GUI. Caregiver contact GUI 254 can be substantially the same as user contact GUI 244 and can include one or more of text, phone, video, and email capability for contacting the user as well as, in some examples, others that the caregiver can wish to contact to relay the user alert information to. Caregiver contact GUI 254 can include message display 612 for displaying text messages, a virtual keyboard 614, and close button 616 for closing the GUI.

FIGS. 7A and 7B illustrate exemplary wearable sensor and wearable speech databases (FIG. 2). As shown in FIG. 7A, wearable sensor database 228 can include, in one example, a row for each time data is recorded, and columns for each sensor type. In the illustrated example, data is recorded every 20 minutes, however, a variety of other intervals can be used. In alternative embodiments, wearable sensor database 228 can include separate tables for various ones of the sensor readings, which can allow for the time interval between data points to be varied for specific sensors to optimize the time interval by sensor type. For non-limiting examples, in some cases, more data can be desirable for the accelerometer(s) than for the weather sensor. In addition, in alternative embodiments, the types and numbers of sensors can be varied. As shown in FIG. 7B, wearable speech database 226 can include data from one or more speech sensors, and can also include results from analysis of the data that can have been performed by speech sensors 222 or other software on or external to wearable device 202. For example, the analysis results can include an analysis of the speech data to determine if the recorded sounds represent a conversation with another person, or background ambient noise, including from a television or radio, or if the user is talking out loud by him or herself. The results of such analysis can be stored in speech database 226, for example, in the "type" column. Speech database 226 can also include one or more cumulative data columns which can be used by the alert database. In the illustrated example, the database includes three cumulative data columns related to information obtained from the speech sensor(s), including percent of interaction with another person, percent of time speaking, and percent of time watching television. In the illustrated example, data from the sensor is stored in the database every twenty minutes and the cumulative data is based on the previous hour of data. In other examples, other time intervals and other durations of time for the cumulative data can be used.

FIG. 8 shows an example network location database (FIG. 2). As shown, the network location database 260 can include GPS location and radius or Geo fence for a given location and a unique identifier linking the location to a table in the network alert database 258 (FIG. 9 shows exemplary network alert databases that can be associated with the GPS locations.) Thus, the exemplary network location database 260 can store geolocation information for a specific user for a variety of locations and can use the information to determine the appropriate alert database for a specific user. As shown in FIG. 9, the network alert database 258 can include a plurality of location-based well-being alert databases for specific geographic locations for a specific user. As described above, an alert database in a wearable device can be configured to be continuously or periodically updated based on a current geographic location of the wearable device. For example, if wearable device 202 is at a GPS location associated with the nursing home, wearable device alert database 230 can receive the nursing home database 902 from the network alert database 258. If the user then leaves the nursing home and travels to the hospital, wearable device alert database 230 can be cleared and then updated with the hospital network alert database 904. Thus, the sensitivity of the wearable device well-being alerts can be varied with user location by uploading different location-based alert databases having different body sensor threshold values. Such an approach can allow for optimizing the sensor reading thresholds and/or combinations of sensor readings that give rise to an alert in a given location. For example, an alert can be triggered at lower thresholds when the user is in a location that is known to create anxiety for the user, such as group gatherings, and thresholds can be raised in other situations where caregiver intervention is less needed, or not as readily available. In the illustrated example, each of the network databases includes the same two data types—pulse and speech type with corresponding alert levels and associated actions or warnings for the user and caregiver alert GUIs. In other examples, many other datatypes in addition to, or instead of, the data types shown can be used. Also, the datatypes can vary by location so that the most relevant sensor data types for expected warning conditions for a given location can be monitored. In yet other examples, a wearable system can analyze and compare all available data regardless of geolocation and only the thresholds for determining if an alert condition has occurred can vary among locations and the threshold data set can be the only information that is transmitted from network alert database 258. As will be appreciated, the number of locations in network alert database 258 can be virtually unlimited, and can include locations created by the caregiver(s) as well as locations created by the user. FIG. 10 shows an example of wearable alert database 230 when the user is located at a GPS location associated with a nursing home alert database 902. For example, the nursing home alert database 902 shown in FIG. 10 can be the same as the nursing home database 902 in the network alert database 258 shown in FIG. 9, and can have been received from the network alert database 258 when the user was located in a geographic location within the geo fence of the GPS location associated with the nursing home stored, for example, in the network location database 260 (FIGS. 2 and 8).

Figure 11:
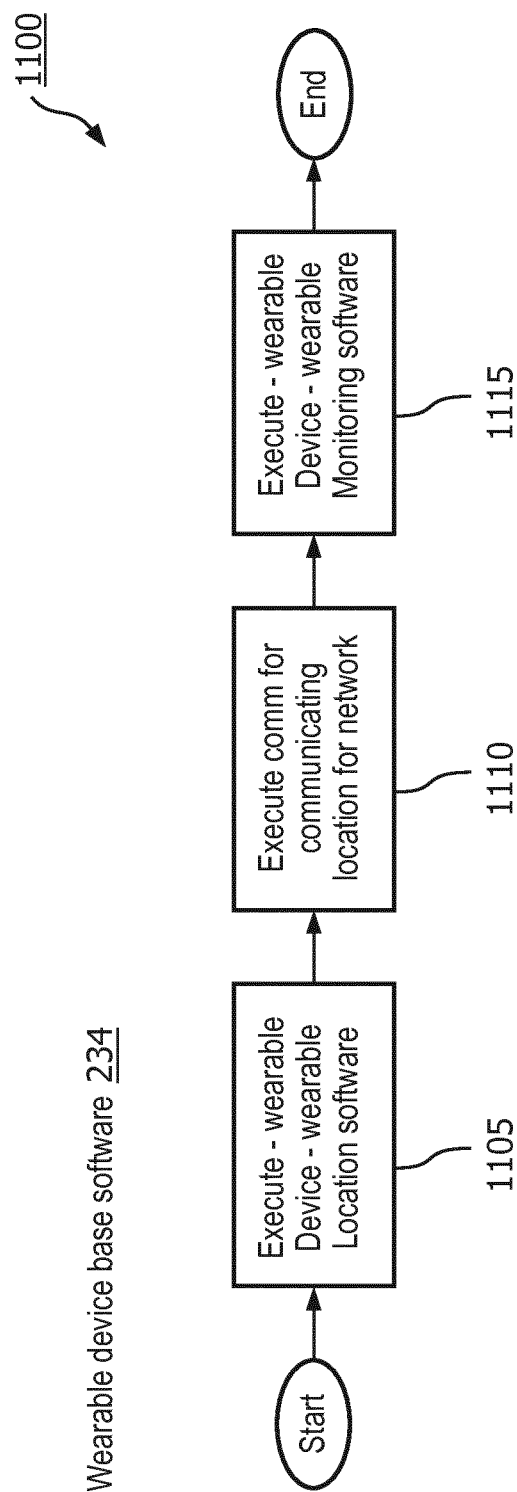
FIG. 11 shows an example algorithm for a wearable device base software, according to an embodiment of the present invention.

FIG. 11 shows example functionality 1100 for base software 234 of wearable device 202 for performing one or more of coordinating and executing various software on the wearable device, coordinating and operating various components of the device, and communication with external system components, such as the network and caregiver device. As shown, some of the base software functions can include, at step 1105 executing wearable device location software 236 for determining current location at step 1110, executing the device communication module 210 for transmitting location information to network 206 and requesting location-specific alert data, and, at step 1115, executing wearable device monitoring software 232 for monitoring sensor data and comparing the sensor data to the alert database to determine if an alert condition has occurred.

Figure 12:
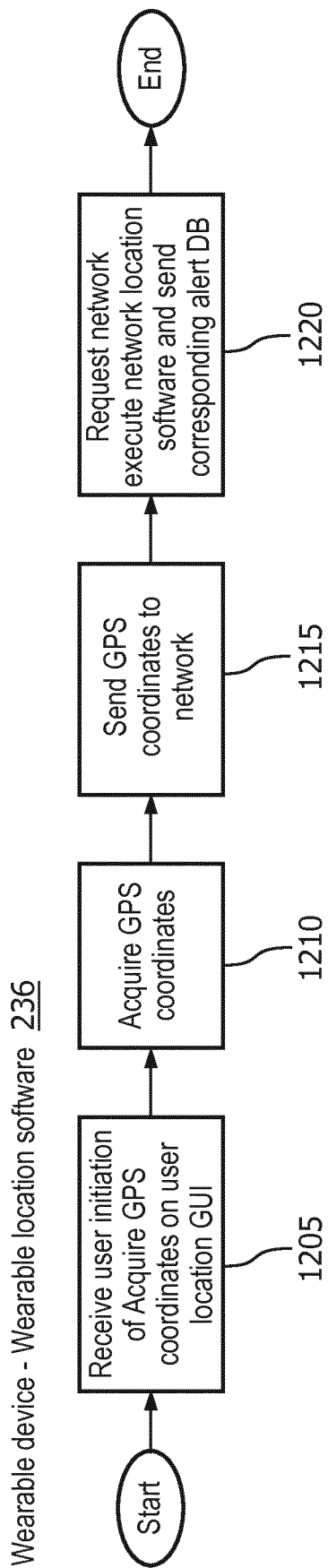
FIG. 12 shows an example algorithm for a wearable location software, according to an embodiment of the present invention.
Figure 13:
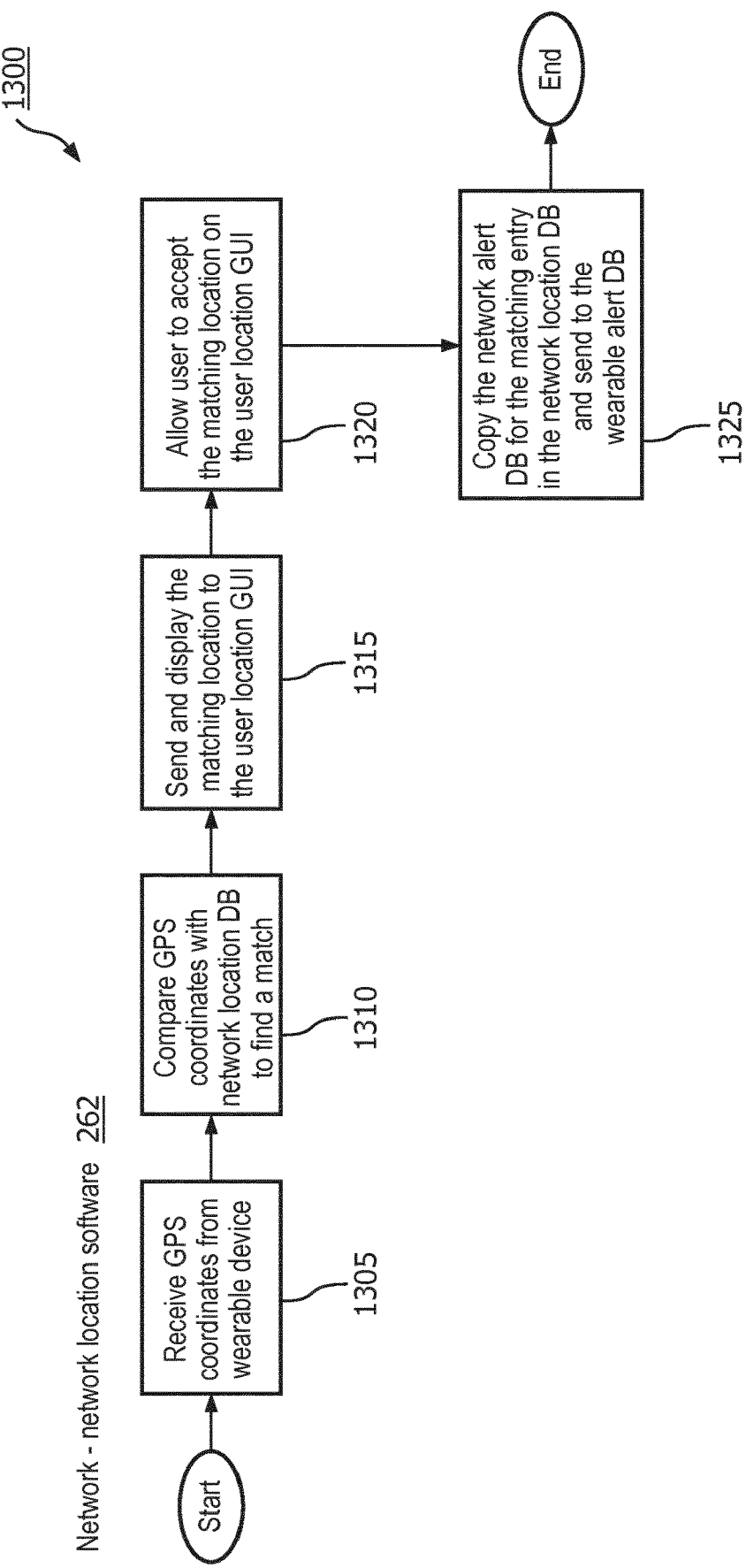
FIG. 13 shows an example algorithm for a network location software, according to an embodiment of the present invention.

FIG. 12 illustrates example functionality 1200 for wearable device location software 236 module (FIG. 2). As shown at step 1205, location software on wearable device 202 can be configured to display a wearable location GUI 238 and receive an instruction from a user to initiate acquisition of location information. At step 1210, location software 236 can also be configured to acquire GPS coordinates from a GPS device, and at step 1215 send the GPS coordinates to network 206. At step 1220, location software 236 requests the network to execute the network location software 262 and return the corresponding alert database. FIG. 13 shows example functionality 1300 for the network location software 262, which can be executed at step 1305 when network 206 receives the GPS coordinates from the wearable device. As shown, at step 1310 network location software can be configured to receive wearable device 202 geolocation information and compare the information to the network location database to determine if there is a match, and if so, at step 1315 the matching location is sent to wearable device 202 for display on the wearable location GUI 238 for confirmation by the user. After the user verifies the location at step 1320, the network alert database corresponding to the matching location can be transmitted to the wearable device at step 1325. In alternative embodiments, the network cannot request user verification of location and can instead immediately send the alert database for a wearable device current location.

Figure 14:
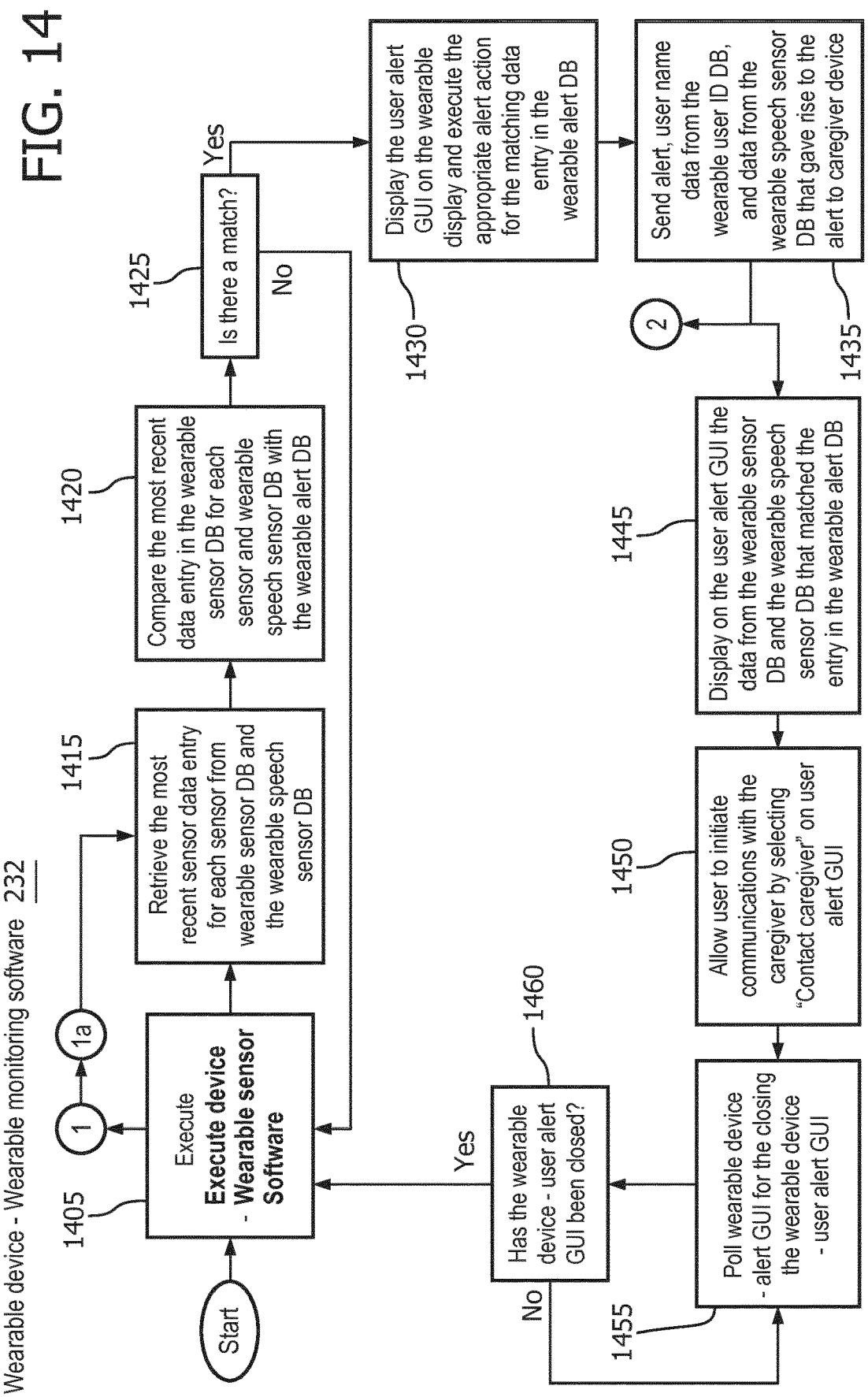
FIG. 14 shows an example algorithm for a wearable monitoring software, according to an embodiment of the present invention.

FIG. 14 illustrates exemplary functionality 1400 for wearable device monitoring software 232. As shown, monitoring software 232 can perform a variety of functions associated with determining if current sensor data indicates an alert condition and for issuing an alert to the user and one or more caregivers. As provided in further detail in FIG. 14, monitoring software 232, upon execution at step 1420, can be configured to execute the wearable sensor software 240, which is represented by a "1" in FIG. 14 and described in more detail in FIG. 15, and then, at step 1415 retrieve sensor data from sensor database 228 and at step 1420 compare the data with the information in wearable alert database 230 to determine if there is a match (1425) and that one or more of the alerts have been triggered. As shown, software 232 can continue to compare updated sensor data to the alert settings until there is a match indicating the user's emotional well-being is compromised. If there is a match, at step 1420 the program can display user alert GUI 242 with the appropriate message and at step 1435 can also send an alert along with user ID information and a copy of the sensor readings giving rise to the alert to one or more caregiver devices 208. Caregiver device(s) 208 can then perform further operations after receiving the alert, which is represented by a "2" in FIG. 14 and further described below in connection with FIG. 16. At step 1445, after sending information to caregiver device(s) 208, monitoring software 232 can, in response to a request from the user, display the sensor data, including, for example, the speech sensor data and other data that gave rise to the alert and can also, in response to a request from the user, display the user contact GUI 244 and at step 1450 initiate a communication request with a specified caregiver. At step 1455 the device can continue to display alert GUI 242 and/or contact GUI 244 until monitoring software 232 receives an instruction from the user to close the GUI (1460), in which case, the program can return to "Start" and begin to monitor new sensor data for another warning state.

Figure 15:
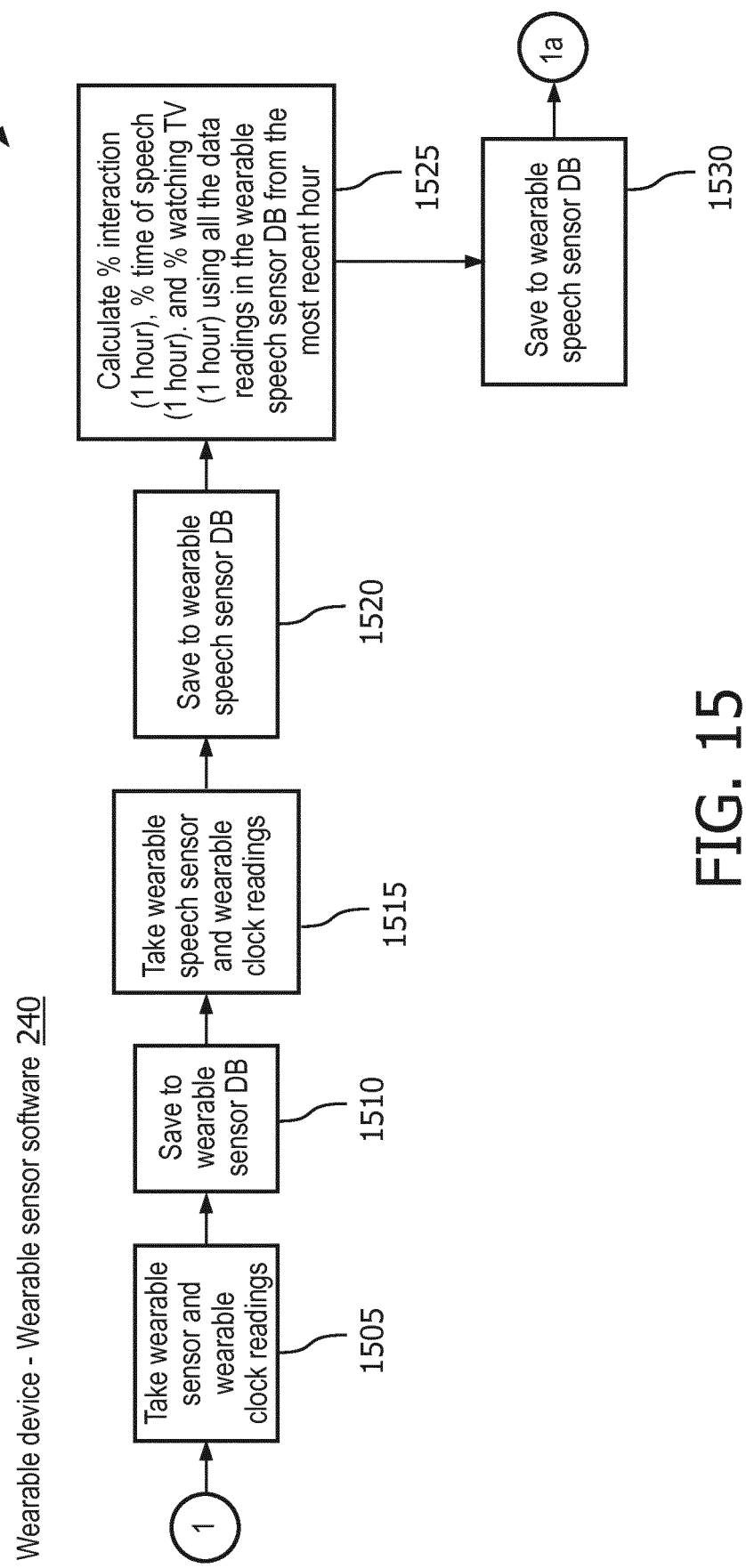
FIG. 15 shows an example algorithm for a wearable sensor software, according to an embodiment of the present invention.

FIG. 15 shows example functionality 1500 for wearable sensor software 240, which can be called by monitoring software 232, for example, at "1" in FIG. 14 discussed above. As shown, at step 1505 sensor software 240 can be configured to continuously or intermittently take readings of wearable sensors 218(1)-218(n) and wearable clock 214, and at step 1510, save those readings to wearable sensor database 228. At step 1515, sensor software 240 can take readings from wearable speech sensor(s) 222 and wearable clock 214, and at step 1520, save those readings to wearable speech sensor database 226. At step 1525 sensor software 240 can also calculate cumulative data based on the acquired sensor data and time information, such as percent of time interacting, speaking, watching TV, etc., over any predetermined period of time, e.g., 1 hour. At step 1530, sensor software 240 can also save the calculated cumulative data to the speech sensor database 226 for analysis by monitoring software 232, beginning at "1a" in FIG. 14 above.

Figure 16:
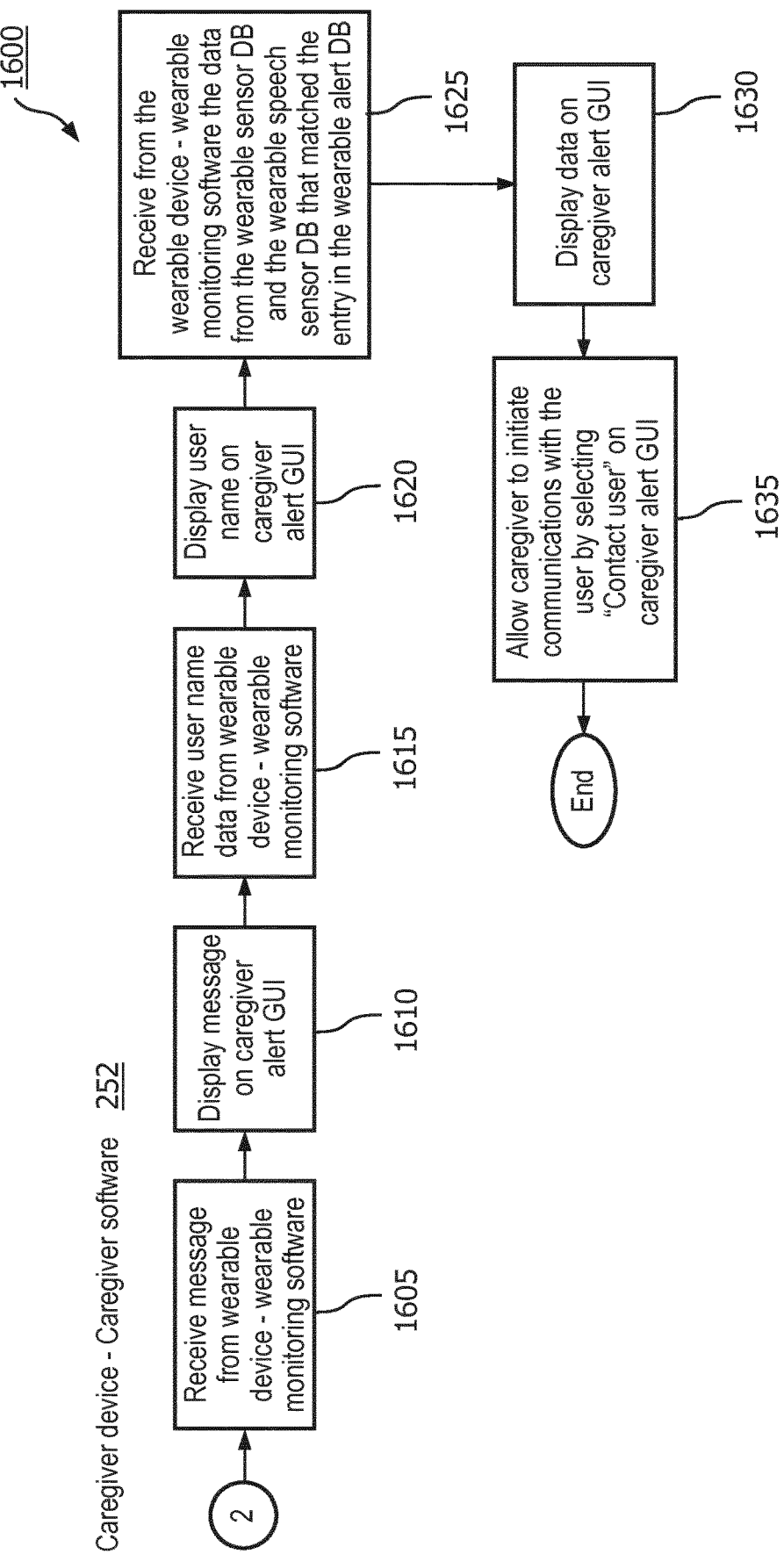
FIG. 16 shows an example algorithm for a caregiver device software, according to an embodiment of the present invention.

FIG. 16 shows example functionality 1600 for caregiver software 252, which can be executed after receiving an alert from a user device, represented as "2" in FIG. 14 above. As shown in FIG. 16, at steps 1605-1620 caregiver software 252 can be configured to receive an alert message from user device 202, along with a user ID, and the sensor data that gave rise to the alert and display the information on caregiver alert GUI 246. At step 1625, software 252 can receive data from wearable sensor database 228 and wearable speech sensor database 226 and at step 1630, display the data on caregiving alert GUI 246, and at step 1635, allow the caregiver to initiate communications with the user by selecting "Contact User" on caregiver alert GUI 246.

Embodiments of the present disclosure include exemplary methods of providing a wearable health system comprising a wearable device 202, a caregiver user device 208, and a network 206. In some embodiments, the exemplary process can include executing software on wearable device 202 for determining location information, executing software on the network 206 for providing wearable device 202 with location-specific alert information, and executing various software modules described herein for using wearable device 202 to monitor for an alert state, and once an alert is triggered, for communicating the alert to the user and the caregiver along with additional information and further options.

Any one or more of the aspects and embodiments described herein can be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules can also include appropriate hardware for assisting in the implementation of the machine executable instructions of the software and/or software module.

Such software can be a computer program product that employs a machine-readable storage medium. A machine-readable storage medium can be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software can also include information (e.g., data) carried as a data signal on a data carrier, such as a carrier wave. For example, machine-executable information can be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device can include and/or be included in a kiosk.

Figure 17:
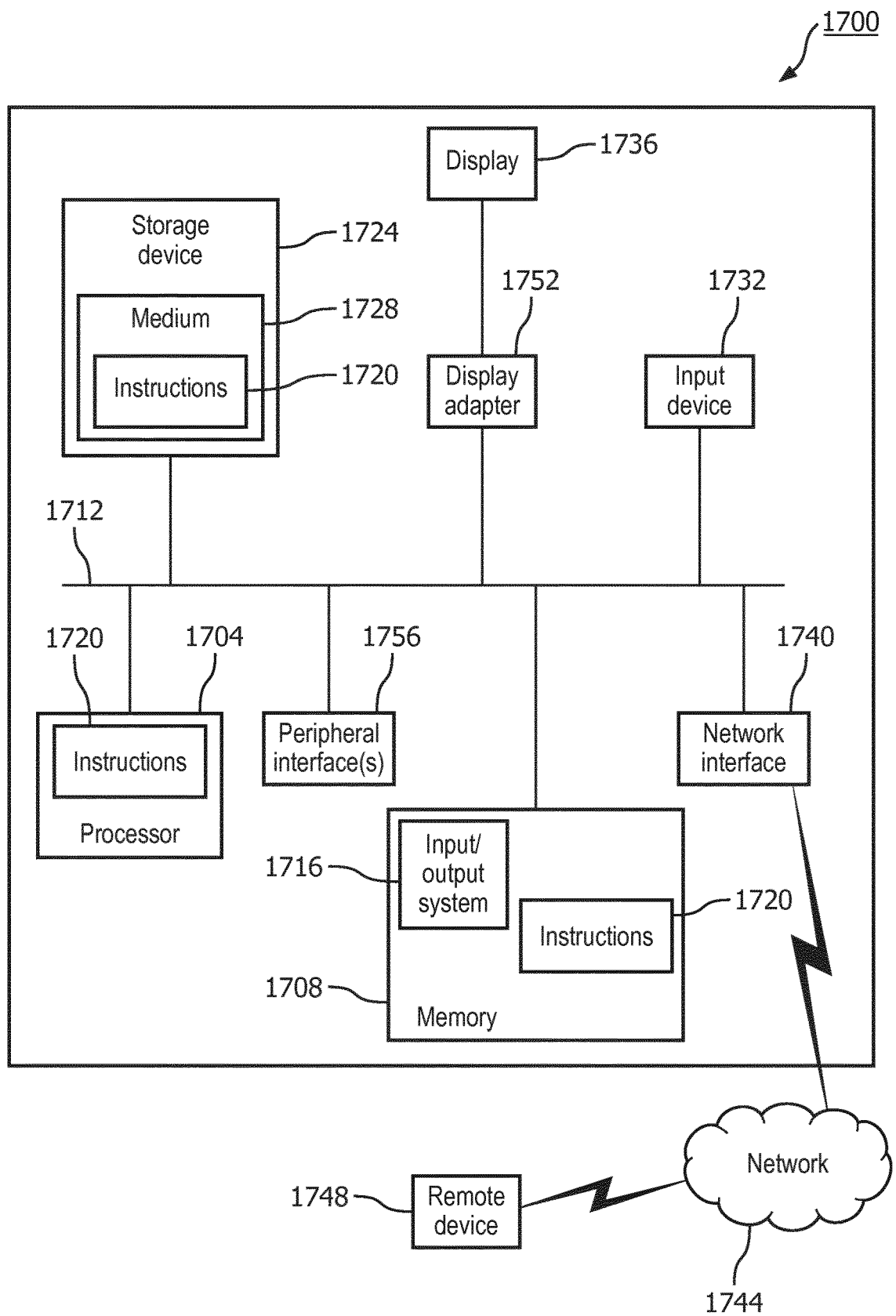
FIG. 17 is a block diagram of a computing system that can be used to implement any one or more of the methods disclosed herein and any one or more portions thereof, according to an embodiment of the present invention.

FIG. 17 shows a diagrammatic representation of one embodiment of a computing device in the exemplary form of a computer system 1700 within which a set of instructions for causing a control system, such as any one or more of various systems of the present disclosure, such as the systems illustrated in other figures of this disclosure, as well as systems that would be apparent to those of ordinary skill in the art after reading this entire disclosure, to perform any one or more of the aspects and/or methodologies of the present disclosure can be executed. It is also contemplated that multiple computing devices can be utilized to implement a specially configured set of instructions for causing one or more of the devices to perform any one or more of the aspects and/or methodologies of the present disclosure. Computer system 1700 includes a processor 1704 and a memory 1708 that communicate with each other, and with other components, via a bus 1712. Bus 1712 can include any of several types of bus structures including, but not limited to, a memory bus, a memory controller, a peripheral bus, a local bus, and any combinations thereof, using any of a variety of bus architectures.

Memory 1708 can include various components (e.g., machine-readable media) including, but not limited to, a random access memory component, a read only component, and any combinations thereof. In one example, a basic input/output system 1716 (BIOS), including basic routines that help to transfer information between elements within computer system 1700, such as during start-up, can be stored in memory 1708. Memory 1708 can also include (e.g., stored on one or more machine-readable media) instructions (e.g., software) 1720 embodying any one or more of the aspects and/or methodologies of the present disclosure. In another example, memory 1708 can further include any number of program modules including, but not limited to, an operating system, one or more application programs, other program modules, program data, and any combinations thereof.

Computer system 1700 can also include a storage device 1724. Examples of a storage device (e.g., storage device 1724) include, but are not limited to, a hard disk drive, a magnetic disk drive, an optical disc drive in combination with an optical medium, a solid-state memory device, and any combinations thereof. Storage device 1724 can be connected to bus 1712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1724 (or one or more components thereof) can be removably interfaced with computer system 1700 (e.g., via an external port connector (not shown)). Particularly, storage device 1724 and an associated machine-readable medium 1728 can provide nonvolatile and/or volatile storage of machine-readable instructions, data structures, program modules, and/or other data for computer system 1700. In one example, software 1720 can reside, completely or partially, within machine-readable medium 1728. In another example, software 1720 can reside, completely or partially, within processor 1704.

Computer system 1700 can also include an input device 1732. In one example, a user of computer system 1700 can enter commands and/or other information into computer system 1700 via input device 1732. Examples of an input device 1732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1732 can be interfaced to bus 1712 via any of a variety of interfaces (not shown) including, but not limited to, a serial interface, a parallel interface, a game port, a USB interface, a FIREWIRE interface, a direct interface to bus 1712, and any combinations thereof. Input device 1732 can include a touch screen interface that can be a part of or separate from display 1736, discussed further below. Input device 1732 can be utilized as a user selection device for selecting one or more graphical representations in a graphical interface as described above.

A user can also input commands and/or other information to computer system 1700 via storage device 1724 (e.g., a removable disk drive, a flash drive, etc.) and/or network interface device 1740. A network interface device, such as network interface device 1740, can be utilized for connecting computer system 1700 to one or more of a variety of networks, such as network 1744, and one or more remote devices 1748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1744, can employ a wired and/or a wireless mode of communication. In general, any network topology can be used. Information (e.g., data, software 1720, etc.) can be communicated to and/or from computer system 1700 via network interface device 1740.

Computer system 1700 can further include a video display adapter 1752 for communicating a displayable image to a display device, such as display device 1736. Examples of a display device include, but are not limited to, a liquid crystal display (LCD), a cathode ray tube (CRT), a plasma display, a light emitting diode (LED) display, and any combinations thereof. Display adapter 1752 and display device 1736 can be utilized in combination with processor 1704 to provide graphical representations of aspects of the present disclosure. In addition to a display device, computer system 1700 can include one or more other peripheral output devices including, but not limited to, an audio speaker, a printer, and any combinations thereof. Such peripheral output devices can be connected to bus 1712 via a peripheral interface 1756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above can be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein can be illustrated and/or described as being performed in a specific order, the ordering is highly variable within ordinary skill to achieve various aspects of the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions can be made to that which is specifically disclosed herein without departing from the spirit and scope of the present invention. As one having ordinary skill in the art shall appreciate in view of the teachings provided herein, the term "caregiver", as used herein and the appended drawings and claims, should not be interpreted broadly to include, for example, medical practitioners, mental health specialists, personal health specialists, assistants, volunteers, family members, friends, colleagues and anyone else who may be caring, providing and/or responsible for the well-being of another person.

Further, as one having ordinary skill in the art will appreciate in view of the teachings provided herein, features, elements, components, etc. described in the present disclosure/specification and/or depicted in the appended Figures may be implemented in various combinations of hardware and software, and provide functions which may be combined in a single element or multiple elements. For example, the functions of the various features, elements, components, etc. shown/illustrated/depicted in the Figure can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" or "controller" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, combinations thereof, etc.) which is capable of (and/or configurable) to perform and/or control a process.

Moreover, all statements herein reciting principles, aspects, and exemplary embodiments of the present disclosure, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar functionality, regardless of structure). Thus, for example, it will be appreciated by one having ordinary skill in the art in view of the teachings provided herein that any block diagrams presented herein can represent conceptual views of illustrative system components and/or circuitry embodying the principles of the present invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown. As used herein and the appended claims, the phrase "at least one of X or Y" is intended to be construed as "X and/or Y".

Furthermore, some exemplary embodiments of the present invention can take the form of a computer program product accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk-read only memory (CD-ROM), compact disk-read/write (CD-R/W) and DVD. Further, it should be understood that any new computer-readable medium which may hereafter be developed should also be considered as computer-readable medium as may be used or referred to in accordance with exemplary embodiments of the present invention and disclosure.

Having described preferred and exemplary embodiments of wearable devices having speech pattern as a metric of well-being functionality, and related systems and methods (which embodiments are intended to be illustrative and not limiting), it is noted that modifications and variations can be made by persons having ordinary skill in the art in view of the teachings provided herein, including the appended Figures and claims. It is therefore to be understood that changes can be made in/to the preferred and exemplary embodiments of the present disclosure which are within the scope of the present invention and exemplary embodiments disclosed and described herein.

Moreover, it is contemplated that corresponding and/or related systems incorporating and/or implementing the device or such as may be used/implemented in a device in accordance with the present disclosure are also contemplated and considered to be within the scope of the present invention. Further, corresponding and/or related method for manufacturing and/or using a device and/or system in accordance with the present disclosure are also contemplated and considered to be within the scope of the present invention.

What is claimed is:

1. A method of remotely monitoring emotional well-being of a user with a wearable device having a speech sensor and at least one body sensor comprising:
monitoring speech pattern data from the speech sensor;
monitoring body sensor data from at least one body sensor;
comparing the speech pattern data and the body sensor data to an alert database having a plurality of different emotional well-being alerts, each of the different emotional well-being alerts comprising a message tailored to a unique combination of speech pattern data and body sensor data;
selecting, from the plurality of different emotional well-being alerts based on the comparison, an emotional well-being alert; and
sending, by a communication module, the selected alert message to a caregiver;
wherein said monitoring of speech pattern data includes calculating a non-interaction value based on a percent of time that the user has not spoken, wherein the calculating of the non-interaction value is also based on at least one factor for normalizing the percent of time to a baseline percent of time that the user has not spoken, and wherein the calculating of the non-interaction value is also based on at least one factor depending on a type of non-interaction activity occurring during the time not speaking detected by the at least one body sensor of the wearable device, wherein the type of non-interaction activity detected affects the comparison of the speech pattern data and the body sensor data, the emotional well-being alerts including a depression alert that is triggered when the non-interaction value is less than a minimum non-interaction value and a reading from a body sensor is below a predetermined value; and
said sending the selected alert message includes sending a depression alert message when the depression alert is triggered.

2. The method according to claim 1, wherein the depression alert is triggered when the non-interaction value is less than the minimum non-interaction value and a blood pressure reading from a wearable device blood pressure sensor is less than a minimum blood pressure.

3. The method according to claim 1, wherein the depression alert is triggered when the non-interaction value is less than the minimum non-interaction value and a pulse reading from a wearable device pulse sensor is less than or equal to a minimum pulse.

4. The method according to claim 1, wherein the depression alert is triggered when the non-interaction value is less than the minimum non-interaction value and a heart rate variability reading from a wearable device pulse sensor is less than or equal to a minimum heart rate variability.

5. The method according to claim 1, wherein said calculating the non-interaction value includes:
recording audio data obtained by the speech sensor;
analyzing the audio data to isolate user speech from ambient sound; and
calculating a percent of time that the user has not spoken from the user speech audio.

6. The method according to claim 5, wherein said analyzing the audio data to isolate user speech from ambient sound includes isolating user speech from sounds associated with television sounds, radio sounds, and speech from people other than the user.

7. The method according to claim 1, wherein the at least one body sensor includes a movement sensor for sensing when the user moves, and wherein said monitoring speech pattern data includes not monitoring speech pattern data during a predefined night time period unless the movement sensor senses movement indicating the user is awake.

8. The method according to claim 1, wherein the depression alert is triggered when the non-interaction value is less than the minimum non-interaction value, the reading from the at least one body sensor is below the predetermined value, and a weather value received by the wearable device indicates poor weather.

9. The method according to claim 1, wherein:
the emotional well-being alerts include a stress alert that is triggered when a reading from at least one body sensor is greater than a maximum value and a speech pattern is detected by the speech sensor; and
said sending the selected alert message includes sending a stress alert message when the stress alert is triggered.

10. The method according to claim 9, wherein the speech pattern detected by the speech sensor includes detecting user speech indicating the user is speaking and ambient speech indicating another person is speaking.

11. The method according to claim 10, wherein the speech pattern detected includes detecting a conversation speech pattern when both user speech and ambient speech are detected and analysis of the speech sensor data indicates the user is involved in a conversation, said sending the selected alert message includes sending a stress alert message that the user is engaged in a conversation that is causing stress.

12. The method according to claim 11, wherein the speech pattern detected includes detecting an argument speech pattern when both user speech and ambient speech are detected and analysis of the speech sensor data indicates the user is involved in an argument, said emotional well-being alerts including a conversation stress alert that is triggered when the conversation speech pattern is detected and the reading from the at least one body sensor exceeds a first maximum value, said emotional well-being alerts further including an argument stress alert that is triggered when the argument speech pattern is detected and the reading from the at least one body sensor exceeds a second maximum value that is lower than the first maximum value.

13. The method according to claim 9, wherein the stress alert is triggered when a reading from one of a wearable device blood pressure sensor and a wearable device pulse sensor exceed a corresponding maximum value and a speech pattern is detected by the speech sensor.

14. The method according to claim 9, wherein the reading from the at least one body sensor is at least one of a user heart rate from a wearable device pulse sensor and a user blood pressure from a wearable device blood pressure sensor and the maximum value is at least one of a maximum heart rate and a maximum blood pressure.

15. A system for remotely monitoring the emotional well-being of a user, comprising:
at least one wearable device having:
a speech sensor structured to sense speech pattern data, and
one or more body sensors structured to sense body sensor data; and
at least one computing device having at least one data processor and structured to collect and monitor data; and
wherein the at least one wearable device is configured to at least one of (i) collect and monitor speech pattern data from the speech sensor, or (ii) collect and monitor body sensor data from the one or more body sensors, and wherein the at least one computing device is configured to (i) compare at least one of the speech pattern data or the body sensor data to data from one or more databases having a plurality of different emotional well-being alerts, each of the different emotional well-being alerts comprising a message tailored to a unique combination of speech pattern data and body sensor data, and (ii) determine whether to trigger at least one of the different emotional well-being alerts based on the comparison, and wherein the at least one wearable device is further structured and configured to at least one of store, display, indicate or send an alert message when at least one of the emotional well-being alerts are triggered; and wherein the at least one computing device is configured to (i) calculate a non-interaction value based on a percent of time that the user has not spoken, wherein the calculation is further based on at least one factor for normalizing the percent of time to a baseline percent of time that the user has not spoken, and wherein the calculation is further based on at least one factor depending on a type of non-interaction activity occurring during the time not speaking detected by the at least one body sensor of the wearable device, wherein the type of non-interaction activity detected affects the comparison of the speech pattern data and the body sensor data, and at least one of the emotional well-being alerts includes a depression alert that is triggered when the non-interaction value is less than a minimum non-interaction value and a reading from one or more of the body sensors is below a predetermined value, and (ii) send a depression alert message when the depression alert is triggered.

16. The method according to claim 1, further comprising updating at least one body sensor threshold of the alert database based on a geographic location of the wearable device.

* * * * *